US009968701B2

(12) United States Patent
Thompson, Jr. et al.

(10) Patent No.: US 9,968,701 B2
(45) Date of Patent: May 15, 2018

(54) SCENTED FAN FRAGRANCE DELIVERY SYSTEM

(71) Applicant: Caffco International Ltd., Montgomery, AL (US)

(72) Inventors: James Lamar Thompson, Jr., Montgomery, AL (US); Longwei Zhang, Dongguan (CN)

(73) Assignee: CAFFCO INTERNATIONAL LTD., Montgomery, AL (US)

( * ) Notice: Subject to any disclaimer, the term of this patent is extended or adjusted under 35 U.S.C. 154(b) by 68 days.

(21) Appl. No.: 15/224,045

(22) Filed: Jul. 29, 2016

(65) Prior Publication Data

US 2017/0028090 A1   Feb. 2, 2017

Related U.S. Application Data

(60) Provisional application No. 62/198,493, filed on Jul. 29, 2015.

(51) Int. Cl.
| | |
|---|---|
| *B01F 3/04* | (2006.01) |
| *A61L 9/04* | (2006.01) |
| *A61L 9/12* | (2006.01) |
| *A61L 9/03* | (2006.01) |

(52) U.S. Cl.
CPC .............. *A61L 9/042* (2013.01); *A61L 9/032* (2013.01); *A61L 9/122* (2013.01); *B01F 3/04085* (2013.01); *A61L 2209/12* (2013.01)

(58) Field of Classification Search
CPC ........ B01F 3/04; B01F 3/04085; A61L 9/122; A61L 9/12

USPC ................... 261/30, 104, DIG. 88
See application file for complete search history.

(56) References Cited

U.S. PATENT DOCUMENTS

| | | | |
|---|---|---|---|
| 4,059,422 | A | 11/1977 | Steiner |
| 4,666,638 | A | 5/1987 | Baker et al. |
| 4,707,338 | A | 11/1987 | Spector |
| 4,808,347 | A | 2/1989 | Dawn et al. |
| 5,192,342 | A | 3/1993 | Baron et al. |
| 5,230,867 | A | 7/1993 | Kunze et al. |
| 5,376,338 | A | 12/1994 | Zlotnik |
| 5,431,885 | A | 7/1995 | Zlotnik et al. |
| 5,460,787 | A | 10/1995 | Colon |
| 5,498,397 | A | 3/1996 | Horng |

(Continued)

FOREIGN PATENT DOCUMENTS

| | | |
|---|---|---|
| CN | 203489149 | 3/2014 |
| EP | 925717 | 6/1999 |

(Continued)

OTHER PUBLICATIONS

U.S. Appl. No. 14/690,145, "Notice of Allowance", dated Sep. 18, 2017, 8 pages.

(Continued)

*Primary Examiner* — Robert A Hopkins
(74) *Attorney, Agent, or Firm* — Kilpatrick Townsend & Stockton LLP

(57) ABSTRACT

This application generally relates to systems, devices, and methods for delivering a fragrance. In some embodiments, portable fragrance delivery systems are provided. In further embodiments, improved fragrance delivery systems are provided that provide increased dispersion of scented agents by utilizing a fan formed from a fragrant material.

9 Claims, 13 Drawing Sheets

(56) References Cited

U.S. PATENT DOCUMENTS

| | | | |
|---|---|---|---|
| 5,547,616 | A | 8/1996 | Danes et al. |
| 5,565,148 | A | 10/1996 | Pendergrass, Jr. et al. |
| 7,223,166 | B1 | 5/2007 | Wiseman, Sr. et al. |
| 7,942,388 | B2 | 5/2011 | Suissa et al. |
| 8,137,629 | B2 | 3/2012 | Faber et al. |
| 8,158,066 | B2 | 4/2012 | Yang et al. |
| 8,412,029 | B2 | 4/2013 | Browder et al. |
| 8,724,975 | B2 | 5/2014 | Browder et al. |
| 9,867,896 | B2 | 1/2018 | Thompson et al. |
| 2003/0035729 | A1 | 2/2003 | Chen |
| 2003/0086815 | A1 | 5/2003 | Wesley et al. |
| 2005/0275118 | A1* | 12/2005 | Chen ............... A61L 9/122 261/30 |
| 2007/0025888 | A1 | 2/2007 | Gupte et al. |
| 2007/0207066 | A1 | 9/2007 | Thur et al. |
| 2008/0130266 | A1 | 6/2008 | Dewitt et al. |
| 2009/0200393 | A1 | 8/2009 | Avelar et al. |
| 2010/0001417 | A1 | 1/2010 | D'Amico et al. |
| 2010/0044468 | A1 | 2/2010 | Granger et al. |
| 2011/0027124 | A1 | 2/2011 | Albee et al. |
| 2012/0183280 | A1 | 7/2012 | Kowalec et al. |
| 2013/0049236 | A1 | 2/2013 | Garon et al. |
| 2015/0297774 | A1 | 10/2015 | Thompson et al. |
| 2017/0028090 | A1 | 2/2017 | Thompson et al. |

FOREIGN PATENT DOCUMENTS

| | | |
|---|---|---|
| EP | 962139 | 12/1999 |
| EP | 2287089 | 2/2011 |
| JP | 11216335 | 8/1999 |
| WO | 9510352 | 4/1995 |
| WO | 2012093246 | 7/2012 |
| WO | 2015161266 | 10/2015 |

OTHER PUBLICATIONS

"Scent Fan product in US market", Scent savvy scentique & scent-in http://www.samsclub.com/sams/fragrancers/prod1114-0158.ip http://www.bescentsavvy.com/onlinestorefragraners.html, Jan. 7, 2011, 2 pages.

U.S. Appl. No. 14/690,145, "Restriction Requirement", dated Jan. 11, 2017, 8 pages.

PCT/US2015/026490, "International Preliminary Report on Patentability", dated Oct. 27, 2016, 13 pages.

PCT/US2015/026490, "International Search Report and Written Opinion", dated Jun. 25, 2015, 17 pages.

\* cited by examiner

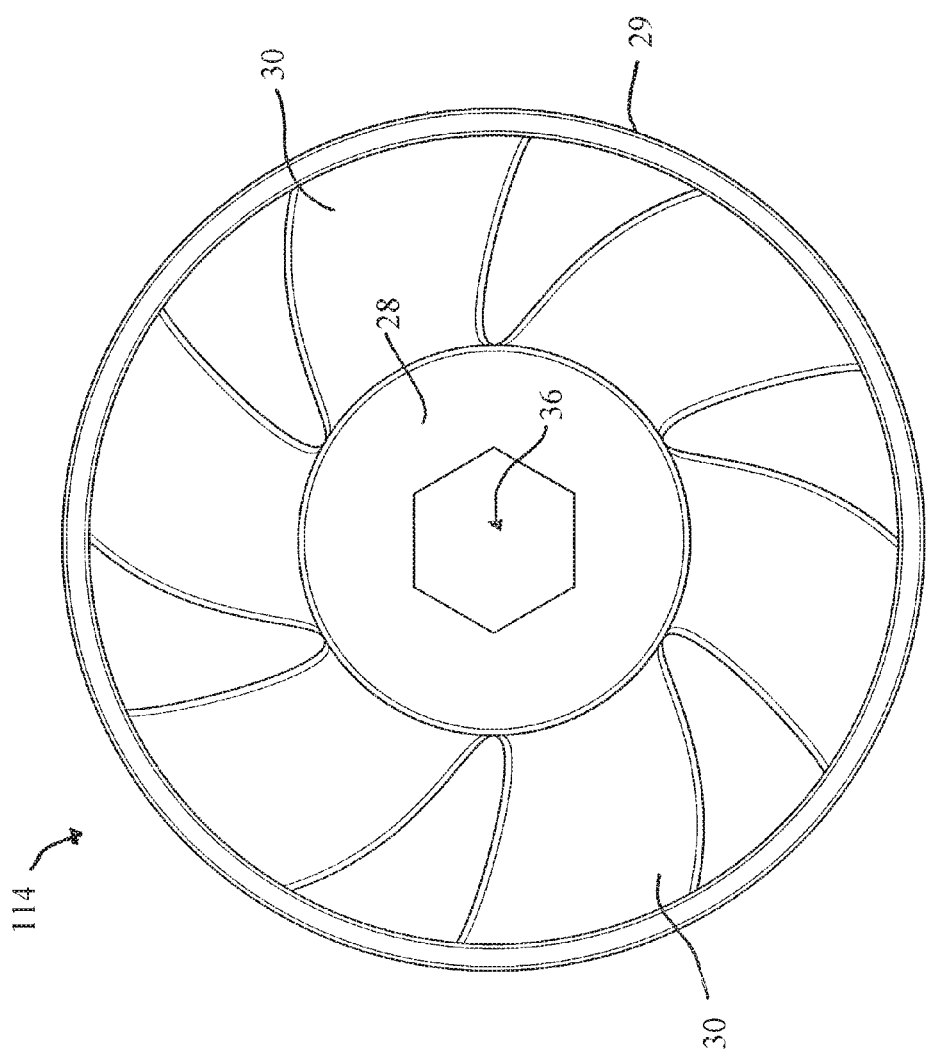

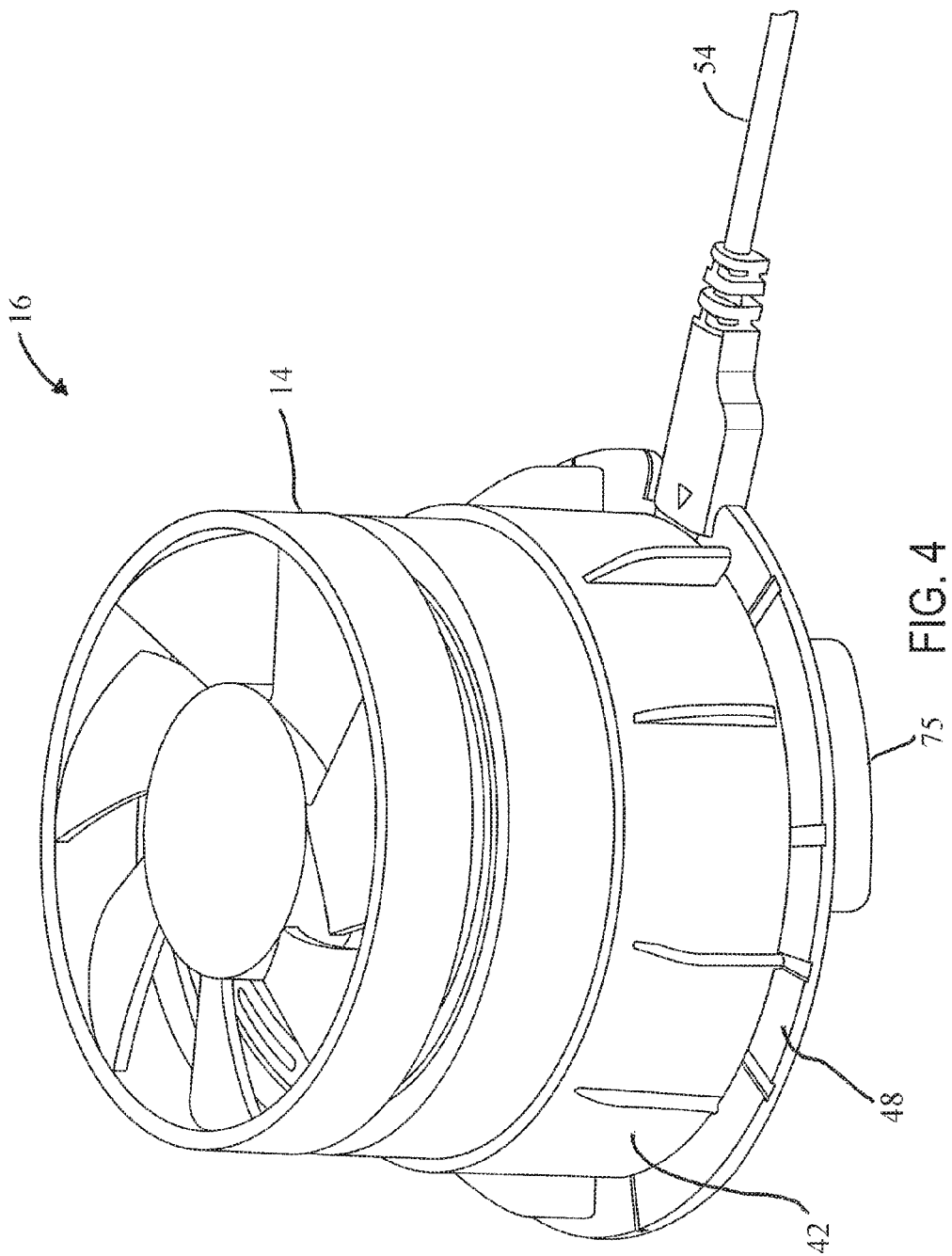

SCENTED FAN FRAGRANCE DELIVERY SYSTEM

CROSS-REFERENCE TO RELATED APPLICATIONS

This application claims priority to and the benefit of U.S. Provisional Patent Application No. 62/198,143 filed on Jul. 29, 2015, the full disclosure of which is incorporated herein by reference in its entirety for all purposes.

FIELD

This application relates generally to systems, devices, and methods for delivering and dispersing a fragrance.

BACKGROUND

Various configurations of fragrance devices have been developed. Typically, such devices use various heat sources, such as a tea light or a heat-producing light bulb, that simultaneously act to emit light and also act to slowly warm wax-based substances that are heavily scented with a fragrance. The heat sources of such devices act to turn the waxy fragrance-scented substance from an initial solid state over time into a liquid state. As the wax-based substance warms up, agents within the substance may be dispersed into the air to spread the scent of the fragrance device.

While prior fragrance systems, devices, and methods have been generally sufficient in dispersing scented agents, further improvements may be desired.

SUMMARY

In some aspects of the present invention, fragrance delivery systems are provided. In some embodiments, a fragrance delivery system described herein includes a motor, a fan including a blade or blades configured to rotate about a fan axis to propel air in a downstream direction from the fan, and a means for powering or delivering power to the motor to rotate the fan blade(s). The fan blade or blades may be made of a fragrant material, or may contain fragrant material, that is released into the air, particularly when the fan blade is rotated. In some embodiments the motor may be powered by batteries positioned in, on or near the motor or, among other alternatives, it may be powered by household current supplied through a conventional electrical cord and plug attached to the motor.

The system of this invention need not necessarily be housed in or include any container, but the system typically will include a decorative vessel, body or container consisting of a vessel made of ceramic, metal, wood, plaster, resin or other appropriate material or combination of materials. Such a container may be esthetically pleasing, may serve to protect and shield the motor and fan blade structure from undesirable contact, and may serve to direct the flow of fragrance emitted by the system among other things.

The fragrance delivery system assembly may include at least a means for forcing airflow through the vessel, such as an electrically powered fan, and a base with or attached to a power source, which may be an electrical cord with plug or a battery and an on/off switch. The electrical cord may be, for example, a standard 110 volt cord or a USB computer cable among other alternatives. Airflow through the fan blade(s) facilitates release of fragrance into the room or other space containing the system. In some embodiments, a lamp or other light source may provide light thru the vessel perforations and or to provide a source of heat. The lamp or light source may be, for example, a LED light. In some embodiments, no light source is included.

The fan blade or blades assembly may be, or may include, for example, fragrance-impregnated molded ethylene vinyl acetate (EVA) plastic. In some embodiments, the fragrance-carrying fan blade may be a fragrance-impregnated molded thermoplastic rubber (TPE) or a fragrance-impregnated molded thermoplastic elastomer (TPE) or any other suitable fragrance-emitting or fragrance carrying material.

The fan blade or blades assembly may be in any form suitable for its intended purpose of forcing air through the blades so that a stream or streams of fragrant air will be emitted by the device.

The fan blade or blades, in some embodiments, may be easily detached from and attached to the assembly so that the blade(s) may be replaced to provide a different fragrance or to provide a replacement source of fragrance when the fragrance in a particular fan blade or blades in use is spent.

Numerous fan blade structures like, or different from, those depicted in the figures may be used. The fan blade(s) may be, or may include, EVA, TPR, or TPE or any other suitable material capable of formation into an appropriate fan blade(s) shape and capable of serving as a carrier for, and capable of releasing into the air, fragrance oils or other fragrance materials. In some embodiments, heat may be used to impregnate the oil into the fan blade materials either before or after it is formed. In some instances, pellets of such material may be impregnated with the fragrance materials before the pellets are molded into the fan blade shape by melting the pellets and forming the melted material in a mold to create the fan blade(s). In some instances, the fragrance delivery system of this disclosure may include a heat source to facilitate and or accelerate release of fragrance from the fan.

As noted above, the fragrance delivery system may include a battery power source. The battery may provide backup power or an alternative power source to ensure the fragrance delivery system is portable. Another embodiment may include, at least a fragrance delivery system without a power cord relying only on battery power.

A shell for housing the fan may be provided. A first end of the shell may have an engagement feature for receiving a partition at the first end of the shell. A light source housing may protrude through a central opening of the partition. An outer surface of the shell may include radially spaced apart ribs projecting outwardly from the shell.

A vessel may be provided that defines an interior volume. The vessel may have an opening and may be configured to receive the shell through the opening of the vessel to position the shell in the interior volume of the vessel. The opening of the vessel may engage with the radially spaced apart ribs of the shell to axially align the vessel with the shell. The vessel may further including a plurality of vents through the vessel to allow air to flow out from the interior volume of the vessel. In some embodiments, a plurality of alternatively selectable vessels may be provided where each of the plurality of vessels have alternative configurations and designs. Each of the plurality of vessels may include an opening configured to receive the shell through the opening to position the shell in the interior volume of the vessel.

In some embodiments, a detachable power cord may be provided. The first end may be configured to detachably couple with a standard outlet (e.g., $12v$ outlet, USB outlet, or the like) and a second end configured to detachably couple with the fan.

In some embodiments, the fragrance delivery system does not include a heater for heating the fragrance carrier. Optionally, the fragrance delivery system does not include a light source. A portable battery may be provided to power the fan. Optionally, the portable battery only powers the fan and may not power any other electronics. In some embodiments, the fragrance delivery system does not include a power cord. Embodiments lacking a heater and/or a light source may be counter-intuitive; however, such embodiments may advantageously last longer on a portable power source and may thus provide extended battery life and a more convenient, moveable, and/or portable fragrance delivery system.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor it is intended to be used in isolation to determine the scope of the claimed subject matter. The subject matter should be understood by reference to appropriate portions of the entire specification of this patent, any or all drawings and each claim. The invention will be better understood upon reading the following description and examining the figures which accompany it.

BRIEF DESCRIPTION OF THE DRAWINGS

FIG. 1A is an exploded view. FIG. 1B is a side view. FIG. 1C is a top view.

FIGS. 3A-3C illustrate various views of exemplary fans according to some embodiments of the present invention.

FIG. 4 is a perspective view of an assembled fragrance delivery device according to some embodiments of the present invention without a vessel.

DETAILED DESCRIPTION

Figure 1A:
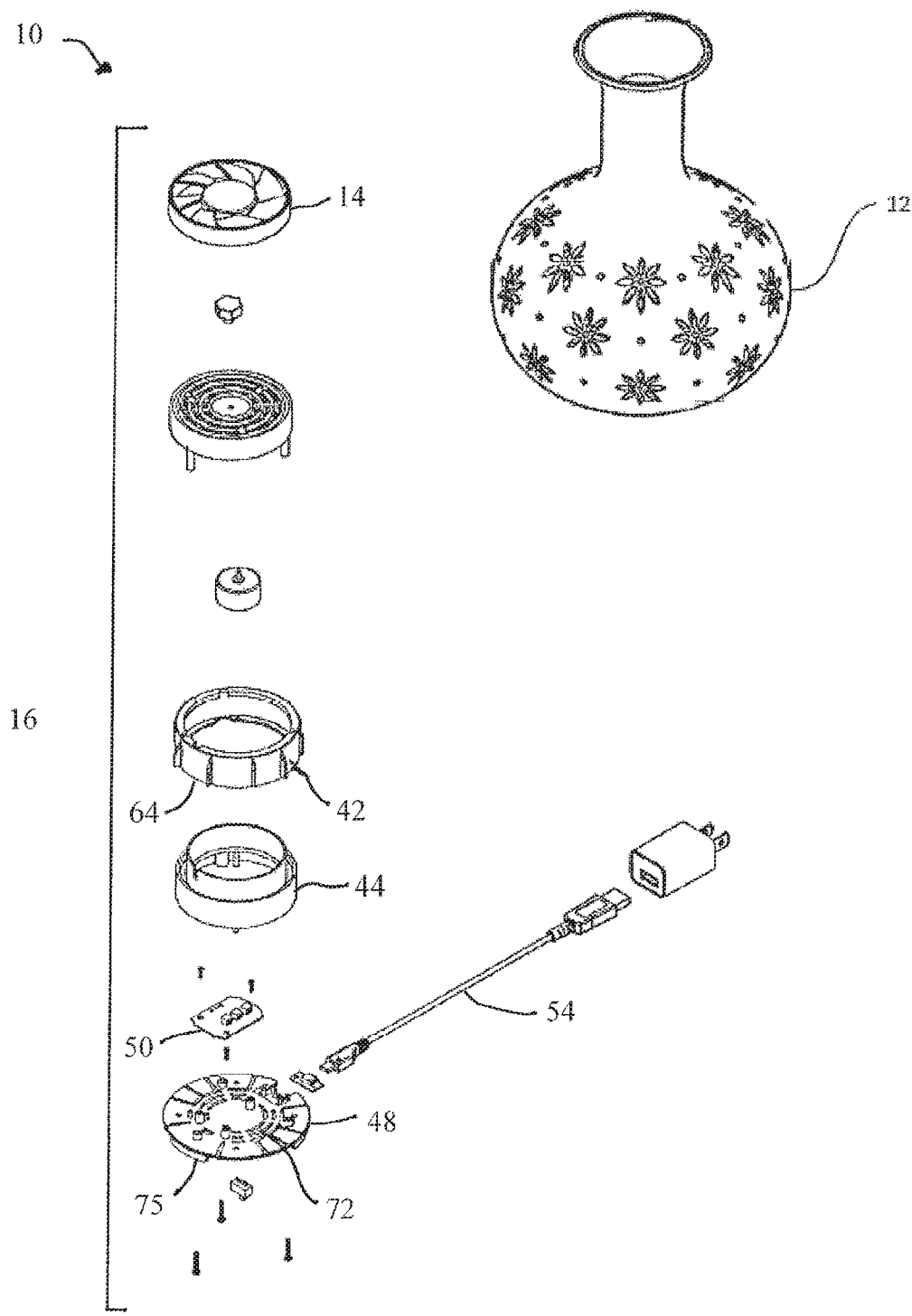
FIG. 1A-1C are various views of exemplary fragrance delivery systems according to some embodiments of the present invention.
Figure 1B:
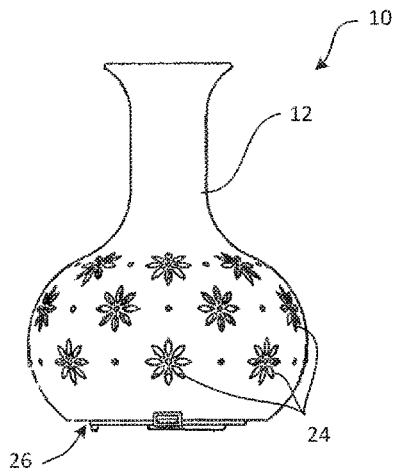
Figure 1C:
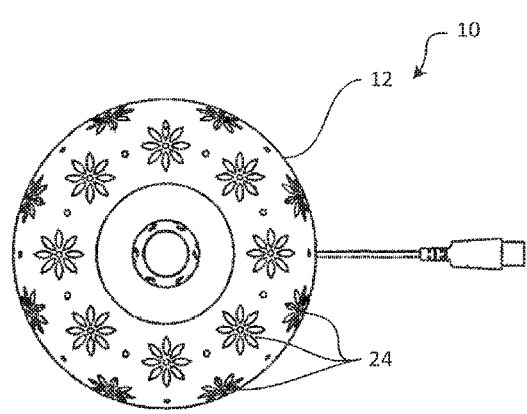
Figure 1D:
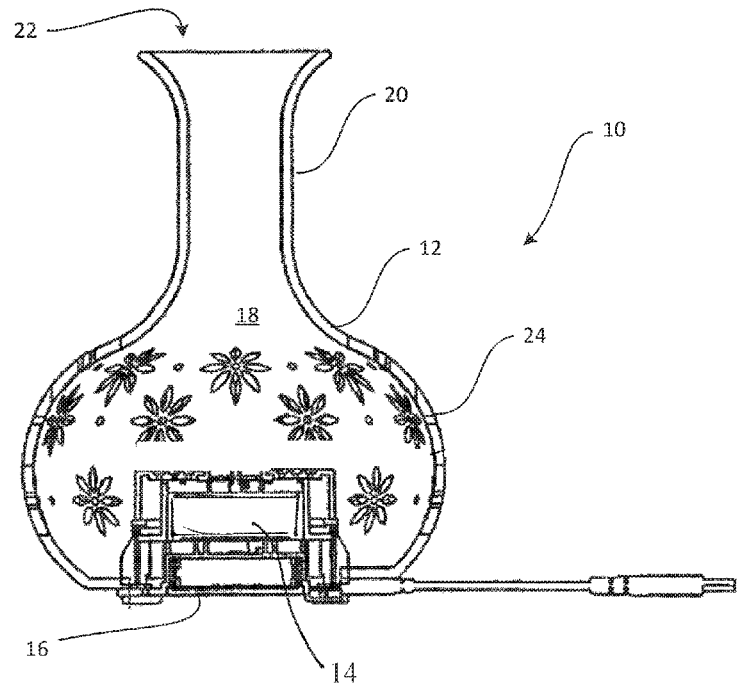
FIG. 1D is a cross sectional view.
Figure 2A:
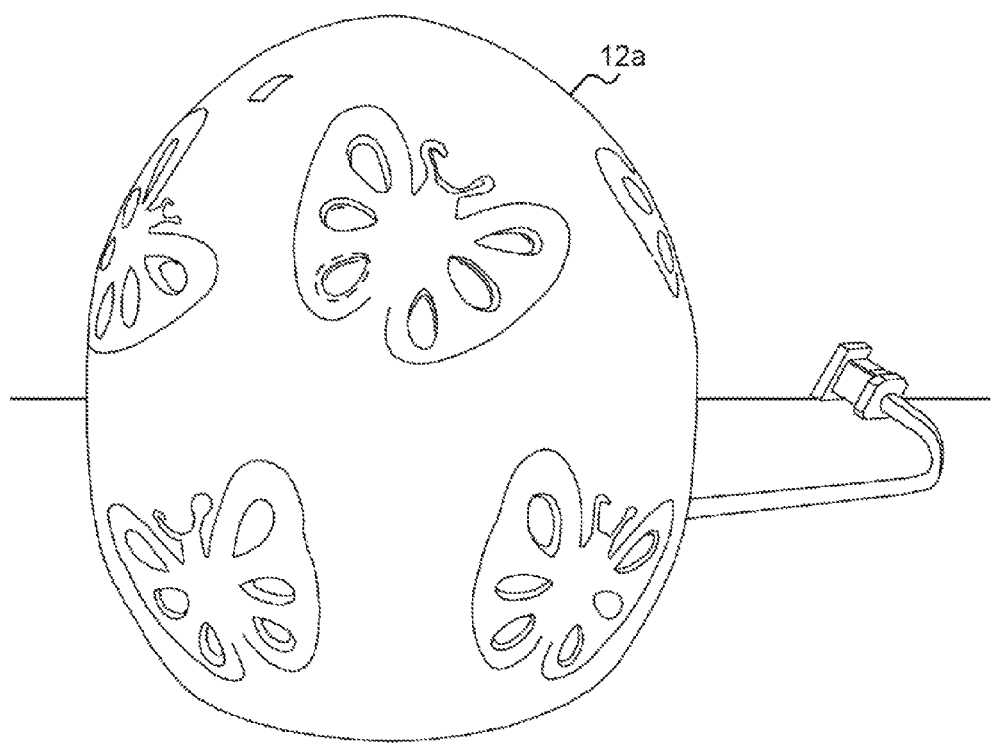
FIGS. 2A-2E illustrate various exemplary vessels that may be used with embodiments of the present invention.
Figure 2B:
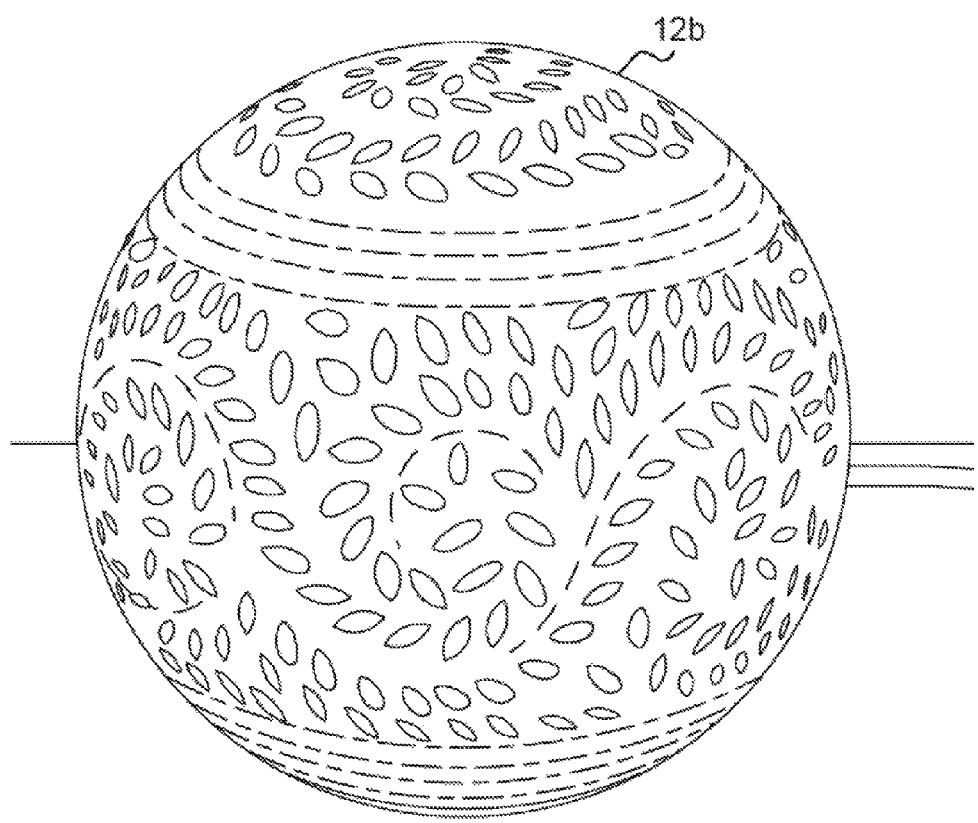
Figure 2C:
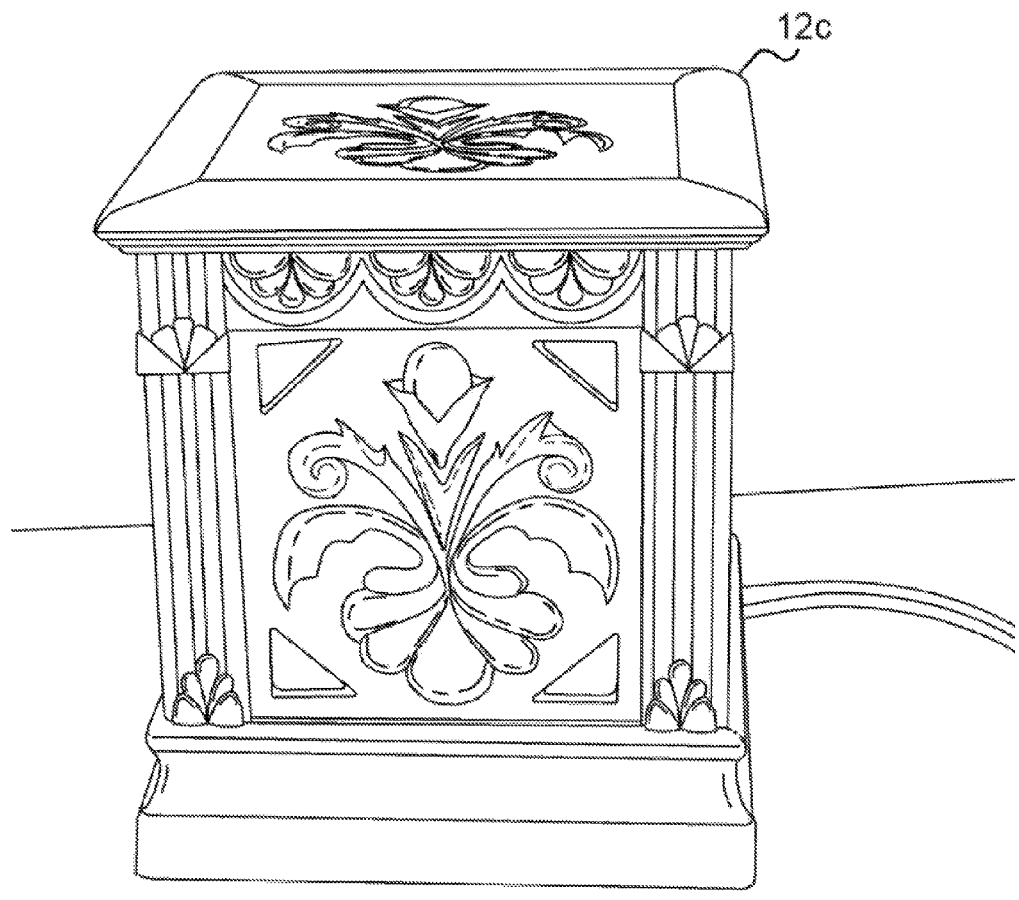
Figure 2D:
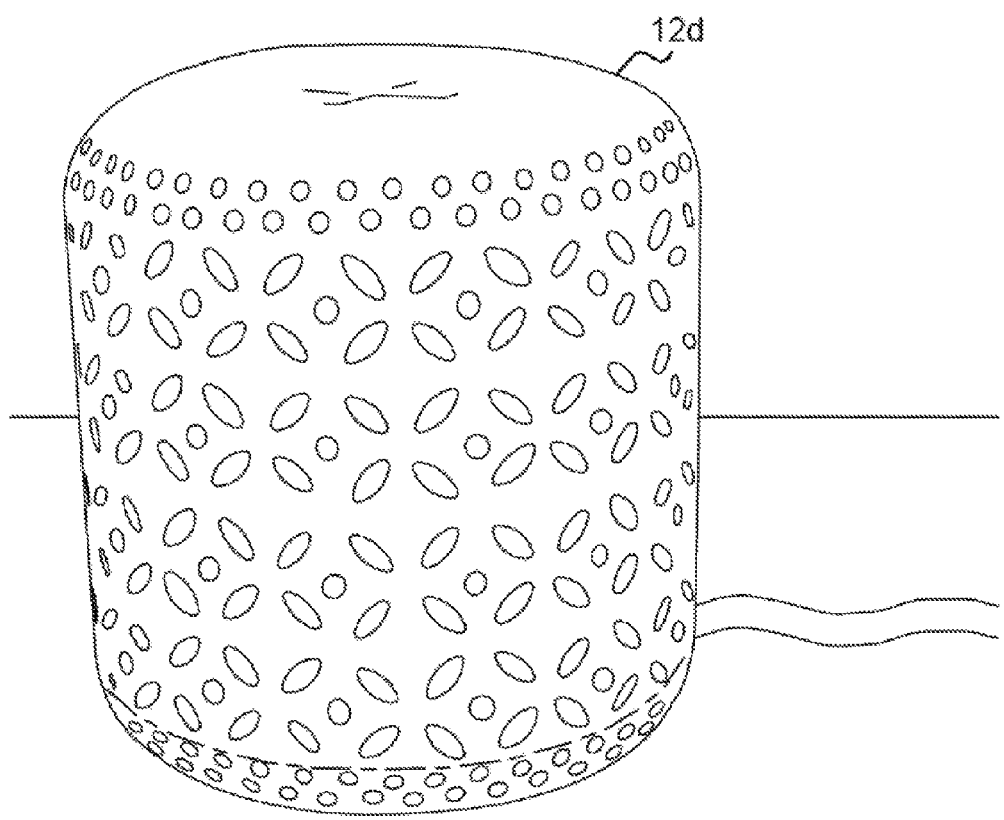
Figure 2E:
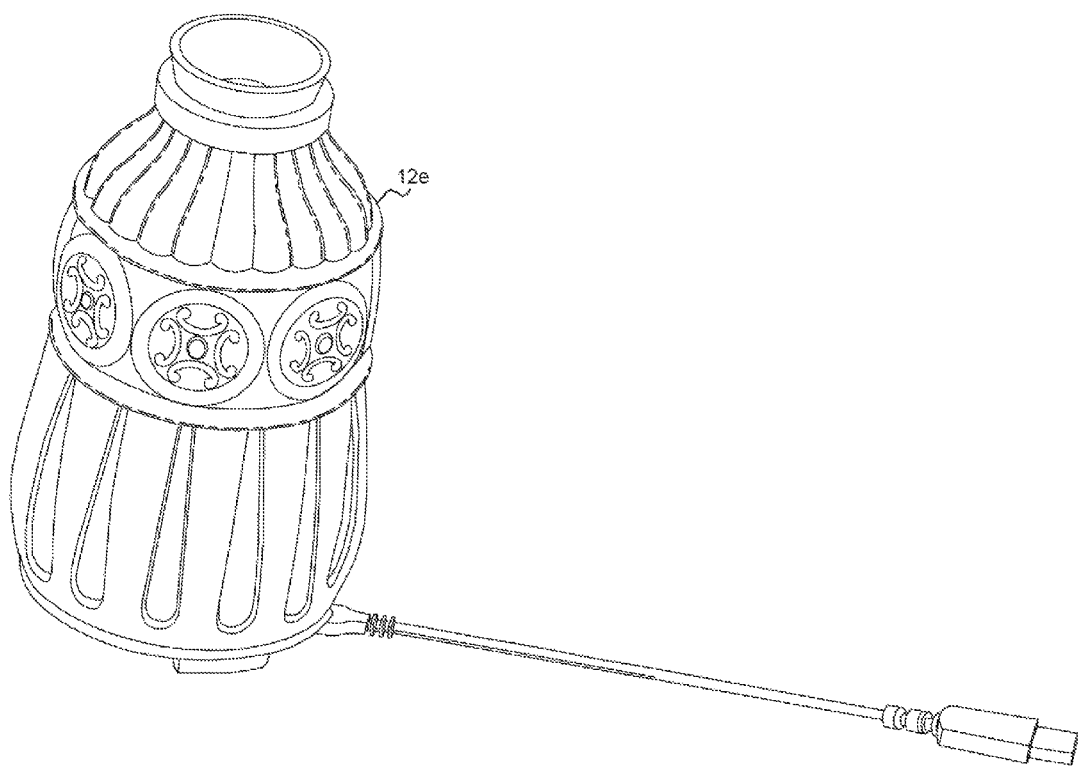

FIGS. 1A-1D illustrate various views of exemplary fragrance delivery systems 10 according to some embodiments of the present invention. FIG. 1A illustrates an exploded view of an exemplary fragrance delivery system 10. FIG. 1B illustrates a side view of the exemplary fragrance delivery system 10. FIG. 1C illustrates a top view of the exemplary fragrance system 10. FIG. 1D illustrates a cross-sectional view of fragrance delivery system 10. Fragrance delivery system 10 includes a vessel 12 configured to house a fragrance delivery device 16 including a fan 14 made of a fragrant material. Vessel 12 defines an interior space 18 for housing the fragrance delivery device 16 and the fan 14. Vessel 12 may have a narrow neck 20 that extends upwardly to a top opening 22. The top opening 22 may allow vaporizing agents or scents released by the fan 14 to move from the interior space 18 of the vessel 12 to the space outside the vessel 12. Additionally, the vessel 12 may include vents or perforations 24 that extend from an interior wall of the vessel 12 to an exterior wall of the vessel 12. The vents or perforations 24 may also allow vaporizing agents or scents released by the fan 14 to exit from the interior space 18 of the vessel 12. In some embodiments, the vents or perforations 24 may also provide a decorative pattern on vessel 12. For example, as illustrated in FIGS. 1A-1D, the vents 24 may be configured to resemble flowers on the surface of the vessel 12. The vents 24 may be placed symmetrically about the vessel 12 to provide a decorative appearance for vessel 12. Vessel 12 may further include a bottom opening 26 opposite the top opening 22 for receiving the fan 14 and the delivery device 16. The side walls of the bottom opening 26 may be configured to couple with the fragrance delivery device 16 to provide releasable engagement between the vessel and the fragrance delivery device 16. The releasable engagement may allow users to interchange fan 14 (e.g., when the fragrant material in a fan 14 is used up, to change the type of fragrance released, or the like). Additionally, this may be beneficial for users who want to switch and interchange between alternative vessels 12 to provide alternative appearances for fragrance delivery system 12. For example, FIGS. 2A-2E illustrate various exemplary vessels 12a-12e that may be used with embodiments of the present invention. Each vessel 12a-12e may include a bottom opening 26 for releasably engaging with the fragrance delivery device 16. The vessels 12a-12e may be decorative and may be made from ceramic, metal, wood, resin or the like.

Figure 3A:
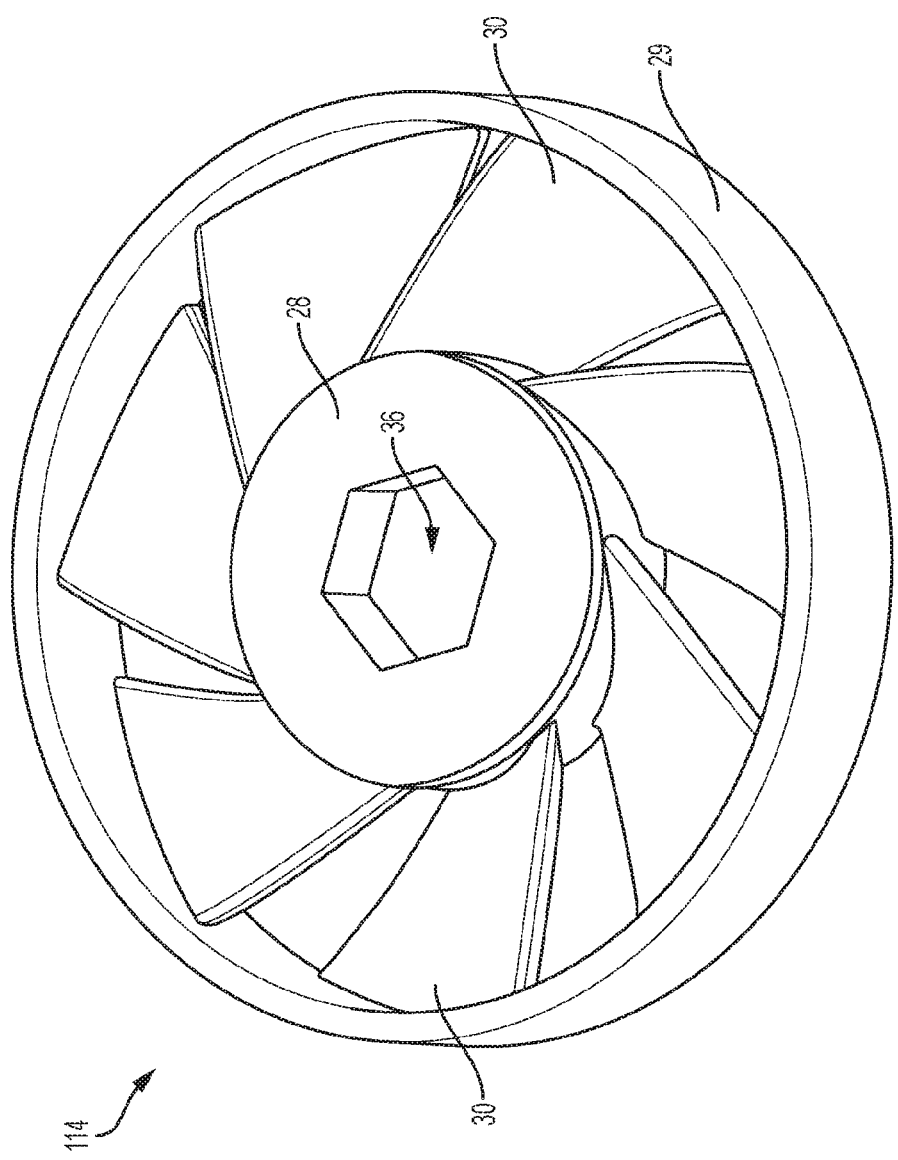
Figure 3C:
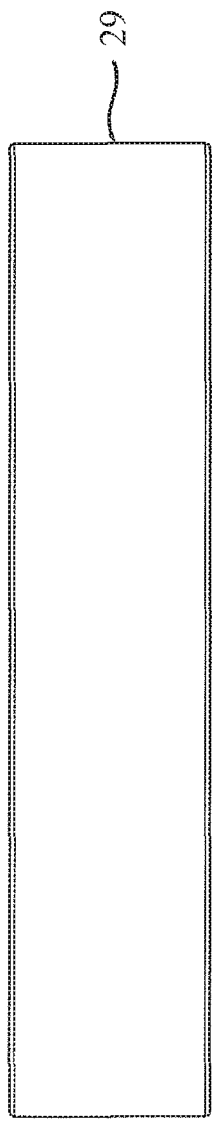
Figure 5A:
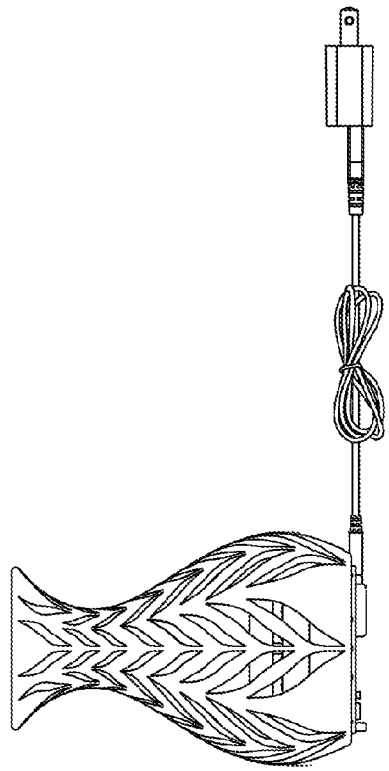
FIGS. 5A, 5B, 5C, 5D, and 5E are first side, second side, top plan, perspective, and perspective views of an assembled fragrance delivery device according to some embodiments of the present invention disposed in a vessel.
Figure 5B:
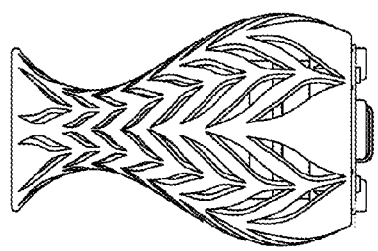
Figure 5C:
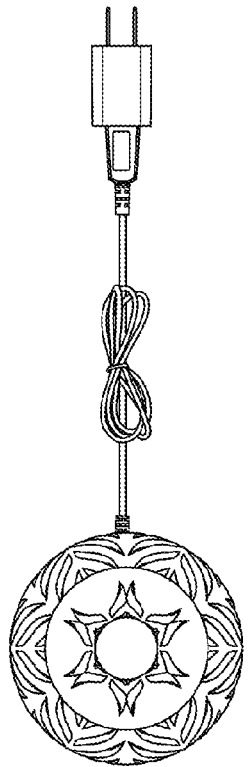
Figure 5D:
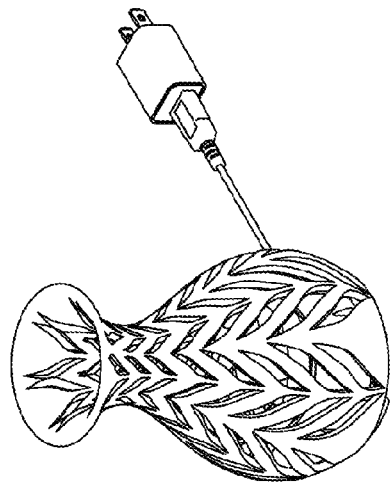
Figure 5E:
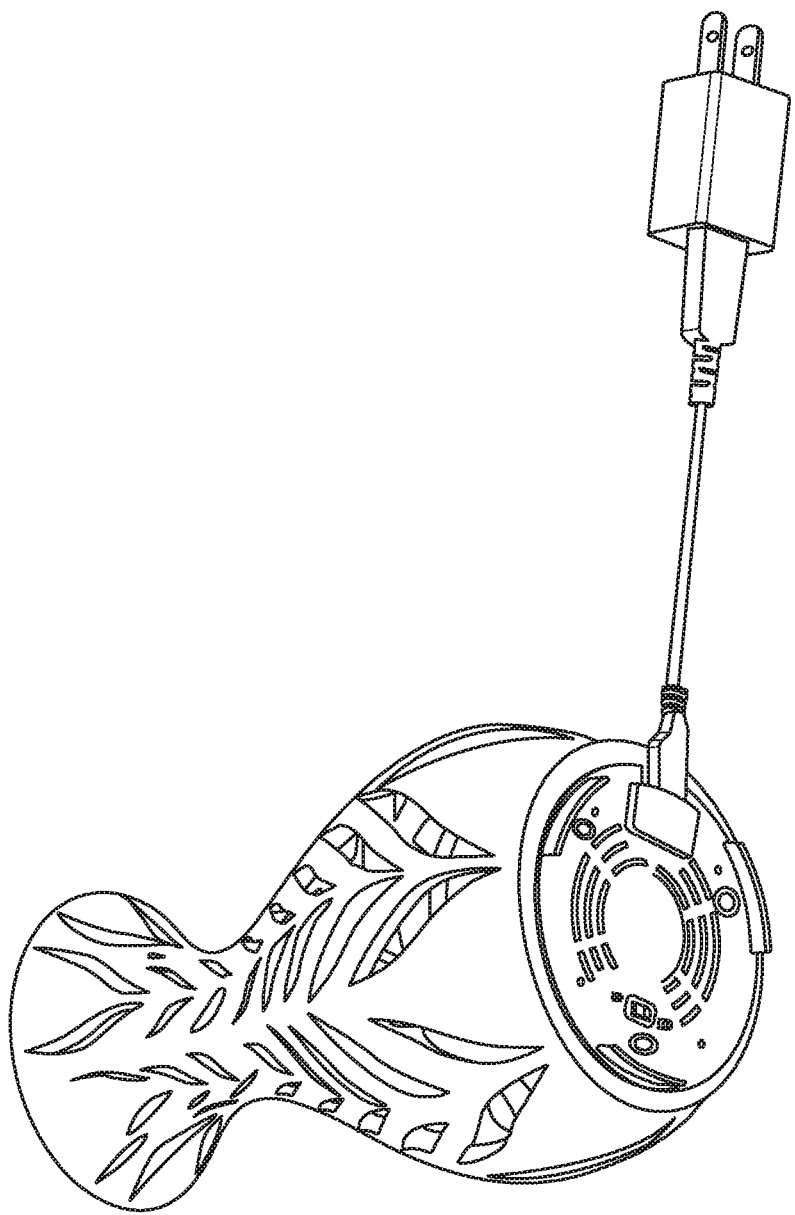

FIGS. 3A-3C illustrate various views of exemplary fans 114 according to some embodiments of the present invention. The fan 114 includes a hub 28 and a plurality of blades 30 connected to the perimeter of the hub 28. The fan also includes a ring around its perimeter connected to the blades 30 and defining a perimeter surface 29. The fan 14 optionally may further include a central opening 36 about central axis 40. FIG. 4 is a perspective view of an assembled fragrance delivery device without a vessel.

The hub of fan 14 is configured to cooperate with the fragrance delivery device 16. In some embodiments, the cooperation between the central opening 36 and the fragrance delivery device 16 may preferentially align the fan 14 with the fragrance delivery device 16, as will be discussed and illustrated further below.

FIG. 4 is a perspective view of an assembled fragrance delivery device 16 according to some embodiments of the present invention without a vessel. FIG. 4 shows a fragrance delivery device 15 according to embodiments of the invention, including a fan 14, a shell 42 on a base 48. The device shown in FIG. 4 includes an optional power cord 54.

FIGS. 5A, 5B, 5C, 5D, and 5E are first side, second side, top plan, perspective, and perspective views of an assembled fragrance delivery device according to some embodiments of the present invention disposed in a vessel.

The fans 14, 114 include a fragrance impregnated solid carrier material. For example, the fan blades may be formed in whole or in part from a fragrance impregnated solid carrier material. In some embodiments, the fragrance impregnated solid carrier material is molded ethylene vinyl acetate (EVA) plastic. The properties of EVA allow it to have absorbed in it, or be impregnated, embedded, or infused with, (collectively referred to herein by use of the term "impregnate" or variations thereof) one or more vaporizing agents, such as for example a fragrance, permitting it to be used as a reservoir for those vaporizing agents. A vaporizing agent is a substance that may be impregnated in a solid carrier material, such as for example EVA, but that is also capable of existing in a substantially vaporized and/or aerosolized state at approximately ambient conditions.

Methods for making and using EVA and other polymeric materials and impregnating them with vaporizing agents such as fragrances, odor-neutralizing substances, insecticides and substances having medicinal properties are known in the art. EVA used in the invention may have a molecular weight in the range of 10,000 Daltons to 100,000 Daltons. Vaporizing agents may be impregnated into the EVA at weight percents varying from 10 to 90%, from 20 to 80% from 30 to 70%, from 30 to 60%, and from 30 to 50%.

As an alternative to EVA, other solid carrier materials may be used to form the fragrance impregnated solid carrier material. For example, in some embodiments, the fragrance impregnated solid carrier material may be a fragrance impregnated molded thermoplastic rubber or a fragrance impregnated molded thermoplastic elastomer (TPE). Alternate embodiments of the solid carrier material may be composed of other polymeric materials including but not limited to, polyethylene (high or low density), polypropylene, polyvinyl chloride, polystyrene, polycarbonate, acrylonitrile butadiene styrene (ABS), polyether block amide (PEBA) and polymethylpentene, ethyl vinyl alcohol, polystyrene, acrylic polymers, polycarbonates, polyurethanes, and nylons.

Possible fragrances to be impregnated in the solid carrier material may be selected from the non-exhaustive list of fragrances including musk oil, civet, castoreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, coconut oil, salvia oil, clove oil, chamomile oil, costus oil, labdanum oil, broom extract, carrot seed extract, jasmine extract, mimosa extract, narcissus extract, olibanum extract, rose extract, acetophenonene and derivatives thereof, dimethylaniline derivatives, naphthaline derivatives, allyl caprate, alpha-amylcinnamic aldehyde, anethole, anisaldehyde, benzyl acetate, benzyl alcohol, benzyl propionate, borneol, cinnamyl acetate, cinnamyl alcohol, citral, citronellal, cumin aldehyde, cyclamen aldehyde, decanol, ethyl butyrate, ethyl caprate, ethyl cinnamate, ethyl vanillin, eugenol, geraniol, exenol, alpha-hexylcinnamic aldehyde, hydroxycitrolnellal, indole, iso-amyl acetate, iso amyl isovalerate, iso-eugenol, linalol, linalyl acetate, p-methylacetophenone, methyl anthranilate, methyl dihydrojasmonate, methyl eugenol, methyl-beta-naphthol ketone, methyl phenyl carbinyl acetate, musk ketol, musk xylol, 2,5,6-nonadienal, gamma-nonalactone, phenyl acetaldehyde dimethyl acetal, beta-phenylethyl alcohol, 3,3,5-trimethylcyclohexanol, gamma-undecalactone, undecenal, vanillin, metoflu-thrin, and mixtures thereof.

Those of skill in the art will recognize that in constructing the solid carrier material for the fan 14, it may also be desirable to mix the fragrance with hindered amines such as for example, 1-(2-hydroxy-2-methylpropoxy)-4-octade-canoyloxy-2,2,6,6-tetramethylpiperidine; 1-(2-hydroxy-2-methylpropoxy)-4-hydroxy-2,2,6,6-tetramethylpiperidine; and bis(1-octyloxy-2,2,6,6-tetramethyl-4-piperidinyl)seba-cate. The foregoing hindered amines may be added to the fragrance at weights of between 0.1% and 2.0% by weight of the EVA (or other carrier), preferably at 0.7% by weight. Further, various antioxidants such as tertiary butylhydroqui-none, butylated hydroxyanisole, phenol bisphosphite, and butylated hydroxytoluene may be added to the fragrance at amounts of between 0.015% and 2.5% by weight of the EVA or other, and preferably between 0.2% and 0.5% by weight.

It is contemplated that in alternate embodiments of the invention, the EVA material used in the solid carrier material may also be impregnated with other vaporizing agents such as an insecticide. The insecticide may be selected from the non-exhaustive list of substances including citronella oil, pyrethrum, aluminum phosphide, and magnesium phosphide. Other alternate embodiments of the invention may also utilize a disc impregnated with vaporizing agents having medicinal properties. Such vaporizing agents having medicinal properties may be selected from the non-exhaustive list of preparations including eucalyptus oil, cinnamon oil, eugenol, geranium oil, peppermint oil, lemongrass oil, menthol, camphor, thymol, turpentine oil, I-desoxyephedrine, and bornyl acetate. In other alternate embodiments of the invention, the foregoing substances may be impregnated in the disc in combination with one or more fragrances or alone.

The fragrance delivery device 16 may further include a light source housed in a light source housing. In some embodiments, the light source does not act as a heat source and does not soften the fragrant material. In some embodiments, no light source is present in the device.

Fan 14 may be centrally supported within the fragrance delivery device 16 and configured to rotate about a fan axis to provide an axial flow of air in a downstream axial direction (upwards and parallel to the fan axis). Power supply 50 may couple with fan 14 to power the fan.

The base 48 may be configured to close off the open end 64 of shell 42 or the bottom end of frame 44. The base 48 may include vents 72. The vents 72 may allow outside air to enter the fragrance delivery device 16 from the bottom of the fragrance delivery device 16. This may provide a continuous supply of air for fan 14 to propel in the downstream direction. In some embodiments, the base 48 further includes feet 75 that may support the base 48 above the support surface to provide clearance for air to be drawn through vents 72 and into shell 42.

In some embodiments, the power supply 50 may be coupled with a power cord 54. The power cord 54 may be an electrical cord with a standard plug for an electrical outlet. In some embodiments, the power cord 54 may be a standard 110 volt cord. In other embodiments, the power cord 54 may be a Universal Serial Bus (USB) to micro-USB or mini-USB plug. In some embodiments, the cord 54 is detachable (during normal user operation) from the power source 50 to provide a more portable fragrance delivery device 16. For example, after recharging a rechargeable battery of the fragrance delivery device 16, a user may detach the cord 54 so as to provide a more compact portable fragrance delivery device 16.

A light source, when present, may be one or more light emitting diodes (LED). In some embodiments the light source and/or transparent housing may provide ambient light through the vessel perforations (e.g., through perforations).

In further embodiments of the invention, the delivery device may not include a light source or light source housing. Embodiments without a light source may be preferable to reduce a power consumption of the device. Additionally it may also be beneficial if the device does not include a heater as a heater may consume a substantial amount of power. By reducing the power consumption of a device, the device may be used for longer periods of time on battery power and without being plugged in.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A fragrance delivery system comprising:
   a fan configured to rotate about a fan axis to propel air in a downstream direction from the fan, wherein the fan comprises a hub and a plurality of blades, and wherein at least a portion of the fan comprises a fragrance impregnated solid carrier material;
   a shell configured to house the fan; and
   a base disposed adjacent to the shell and upstream of the fan, the base having a first surface facing the fan, a second surface opposite the first surface of the base housing, and a plurality of vents defining the inlet of the fan flow path that extend from the second surface of the base housing to the first surface of the base housing, the plurality of vents of the base housing configured to allow air to be drawn by the fan to travel through the base housing and toward the fan.

2. The fragrance delivery system of claim 1, wherein the fragrance impregnated solid carrier material is selected from the group consisting of ethylene vinyl acetate, polyethylene, polypropylene, polyvinyl chloride, polystyrene, polycarbonate, acrylonitrile butadiene styrene, polyether block amide, polymethylpentene, ethyl vinyl alcohol, polystyrene, acrylic polymers, polycarbonates, polyurethanes, nylons, and combinations thereof.

3. The fragrance delivery system of claim 1, wherein the fragrance impregnated solid carrier material comprises ethylene vinyl acetate.

4. The fragrance delivery system of claim 1, wherein the fragrance impregnated solid carrier material comprises a fragrance selected from the group consisting of musk oil, civet, castoreum, ambergris, plant perfumes, sandalwood oil, neroli oil, bergamot oil, lemon oil, lavender oil, sage oil, rosemary oil, peppermint oil, eucalyptus oil, menthol, camphor, verbena oil, citronella oil, coconut oil, salvia oil, clove oil, chamomile oil, costus oil, labdanum oil, broom extract, carrot seed extract, jasmine extract, mimosa extract, narcissus extract, olibanum extract, rose extract, acetophenonene and derivatives thereof, dimethylaniline derivatives, naphthaline derivatives, allyl caprate, alpha-amylcinnamic aldehyde, anethole, anisaldehyde, benzyl acetate, benzyl alcohol, benzyl propionate, borneol, cinnamyl acetate, cinnamyl alcohol, citral, citronellal, cumin aldehyde, cyclamen aldehyde, decanol, ethyl butyrate, ethyl caprate, ethyl cinnamate, ethyl vanillin, eugenol, geraniol, exenol, alpha-hexylcinnamic aldehyde, hydroxycitrolnellal, indole, iso-amyl acetate, iso amyl isovalerate, iso-eugenol, linalol, linalyl acetate, p-methylacetophenone, methyl anthranilate, methyl dihydrojasmonate, methyl eugenol, methyl-beta-naphthol ketone, methyl phenyl carbinyl acetate, musk ketol, musk xylol, 2,5,6-nonadienal, gamma-nonalactone, phenyl acetaldehyde dimethyl acetal, beta-phenylethyl alcohol, 3,3,5-trimethylcyclohexanol, gamma-undecalactone, undecenal, vanillin, metofluthrin, and mixtures thereof.

5. The fragrance delivery system of claim 1, wherein the fragrance impregnated solid carrier material comprises a vaporizing agent.

6. The fragrance delivery system of claim 1, wherein the fragrance delivery system does not include a heater for heating the fragrance carrier.

7. The fragrance delivery system of claim 1, wherein the fragrance delivery system does not include a light source.

8. The fragrance delivery system of claim 1, further comprising a power source, wherein the power source is configured to provide power only to the fan.

9. The fragrance delivery system of claim 1, further comprising a vessel defining an interior volume and having an opening, the vessel configured to receive the fan, the shell, and the base through the opening of the vessel to position the fan in the interior volume of the vessel, wherein the opening of the vessel engages with radially spaced apart ribs of the shell to axially align the vessel with the shell and base, the vessel further including a plurality of vents through the vessel to allow air to flow out from the interior volume of the vessel.

* * * * *